(12) United States Patent
Govari

(10) Patent No.: US 9,833,284 B2
(45) Date of Patent: Dec. 5, 2017

(54) PRESSURE-DRIVEN IRRIGATION PUMP

(71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 75 days.

(21) Appl. No.: 14/613,727

(22) Filed: Feb. 4, 2015

(65) Prior Publication Data

US 2016/0220303 A1   Aug. 4, 2016

(51) Int. Cl.
| | |
|---|---|
| A61M 3/02 | (2006.01) |
| A61B 18/14 | (2006.01) |
| A61M 5/145 | (2006.01) |
| A61B 90/00 | (2016.01) |

(52) U.S. Cl.
CPC ....... *A61B 18/1492* (2013.01); *A61M 3/0254* (2013.01); *A61B 2090/0811* (2016.02); *A61B 2218/002* (2013.01); *A61M 5/145* (2013.01); *A61M 2205/33* (2013.01); *A61M 2205/3334* (2013.01)

(58) Field of Classification Search
CPC ........ A61B 19/00; A61M 5/142; B05B 11/04; B05B 11/0043; B65D 35/28; B65D 35/30
USPC .............................. 604/408; 417/53; 606/33; 623/3.11–3.17
See application file for complete search history.

(56) References Cited

U.S. PATENT DOCUMENTS

| | | | | |
|---|---|---|---|---|
| 1,922,196 A | * | 8/1933 | Butler ................. | F04B 43/0072 417/474 |
| 2,818,815 A | * | 1/1958 | Corneil ................. | A61M 5/142 417/475 |
| 2,915,983 A | * | 12/1959 | Berrian ............... | F04B 43/1207 418/45 |
| 4,058,857 A | * | 11/1977 | Runge ................. | A61M 1/1046 417/412 |
| 4,344,747 A | * | 8/1982 | Henry ........................ | B01J 2/14 264/117 |
| 4,648,877 A | * | 3/1987 | Lundback ........... | A61M 1/1037 623/3.17 |

(Continued)

FOREIGN PATENT DOCUMENTS

| | | |
|---|---|---|
| WO | 96/34205 A1 | 10/1996 |
| WO | 96/34640 A1 | 11/1996 |
| WO | WO 2014/030140 A1 | 2/2014 |

OTHER PUBLICATIONS

European Search Report of European Application No. 16154100 dated Jun. 16, 2016.

*Primary Examiner* — Nathan R Price
*Assistant Examiner* — John Doubrava
(74) *Attorney, Agent, or Firm* — Roberts Mlotkowski Safran Cole & Calderon, P.C.

(57) ABSTRACT

A medical pump includes first and second compartments, which are configured to accept respective first and second containers of fluid to be pumped to a medical device, and a paddle, which is fitted between the first and second compartments. The pump additionally includes a control module, which is configured to drive the paddle to alternate between first time periods in which the paddle applies pressure to the first container so as to pump the fluid therefrom, and second time periods in which the paddle applies the pressure to the second container so as to pump the fluid therefrom.

27 Claims, 3 Drawing Sheets

(56) References Cited

U.S. PATENT DOCUMENTS

| | | | |
|---|---|---|---|
| 4,741,736 A * | 5/1988 | Brown | A61M 5/142 604/131 |
| 5,033,943 A * | 7/1991 | Durrum | F04B 43/086 417/475 |
| 5,056,992 A * | 10/1991 | Simons | A61M 5/14224 417/474 |
| 5,145,338 A * | 9/1992 | Murray | F04B 33/00 417/480 |
| 5,207,355 A * | 5/1993 | Thomsen | A47K 5/1215 222/105 |
| 5,342,313 A | 8/1994 | Campbell et al. | |
| 5,348,539 A * | 9/1994 | Herskowitz | A61M 5/1483 604/141 |
| 5,399,166 A | 3/1995 | Laing | |
| 5,415,532 A * | 5/1995 | Loughnane | F04B 43/082 417/411 |
| 5,554,123 A * | 9/1996 | Herskowitz | A61M 5/1483 604/141 |
| 5,577,891 A * | 11/1996 | Loughnane | F04B 43/082 417/412 |
| 5,681,284 A * | 10/1997 | Herskowitz | A61M 5/1483 604/141 |
| 6,062,612 A * | 5/2000 | Lin | E05B 47/0012 292/142 |
| 6,249,098 B1 * | 6/2001 | Miyazaki | B60S 1/08 15/250.12 |
| 7,118,554 B2 * | 10/2006 | Sibbitt | A61M 5/284 604/191 |
| 8,709,008 B2 | 4/2014 | Willis et al. | |
| 2004/0067700 A1 * | 4/2004 | Kinoshita | B63H 21/213 440/40 |
| 2004/0082915 A1 * | 4/2004 | Kadan | A61B 1/00068 604/164.04 |
| 2008/0215029 A1 * | 9/2008 | Rake | A61M 5/148 604/408 |
| 2010/0209268 A1 * | 8/2010 | Davis | F04B 35/045 417/412 |
| 2010/0211002 A1 * | 8/2010 | Davis | A61M 5/14228 604/67 |
| 2011/0092894 A1 * | 4/2011 | McGill | A61M 1/28 604/29 |
| 2013/0030426 A1 * | 1/2013 | Gallardo | A61B 18/1492 606/33 |
| 2014/0121783 A1 * | 5/2014 | Alley | A61F 2/76 623/33 |
| 2014/0207133 A1 * | 7/2014 | Model | A61B 18/1815 606/33 |
| 2014/0276575 A1 * | 9/2014 | Vanderveen | A61M 5/16827 604/506 |
| 2015/0231518 A1 * | 8/2015 | Rogozinski | A63H 27/10 141/114 |
| 2015/0375714 A1 * | 12/2015 | Umeno | B60S 1/486 15/250.12 |

* cited by examiner

PRESSURE-DRIVEN IRRIGATION PUMP

FIELD OF THE INVENTION

The present invention relates generally to pumps, and specifically to medical irrigation pumps.

BACKGROUND OF THE INVENTION

Irrigation pumps are used in a wide range of apparatus, such as minimally invasive procedures in medical applications. Examples of prior art techniques are provided below.

PCT Patent Publication WO 2014/030140, to Rogozinski, et al., whose disclosure is incorporated herein by reference, describes a fluid transference system, including: (a) at least two inflatable objects; (b) at least one variable-state fluid transfer conduit, interposed between a first and a second inflatable objects, the variable state conduit configured to allow fluid flow there-through in an open state and to disallow the flow in a closed state. Another fluid transfer system includes: (a) an entry port; (b) an exit port; (c) a unidirectional main conduit defined between the entry port and the exit port; (d) an intermediate port; and (e) an intermediate conduit defined between the intermediate port and the main conduit, intersecting the main conduit between a first unidirectional valve and a second unidirectional valve, the main conduit defining a unidirectional fluid flow.

U.S. Pat. No. 7,118,554, to Sibbitt, et al., whose disclosure is incorporated herein by reference, describes a syringe device comprising: a first syringe comprising: a first syringe barrel including a first opening at a distal end thereof through which fluid may be forced or aspirated; and a first syringe plunger sliding within the first syringe barrel for forcing fluid through the first syringe barrel opening, the first syringe plunger including a stopper at a distal end thereof which sealingly and slidably engages the first syringe barrel; a reciprocating member which moves along a track parallel to the axial direction of the first syringe; and a reciprocating device connecting the first syringe plunger to the reciprocating member so that when one member of the group consisting of the first syringe plunger and the reciprocating member moves distally, another member of the group is forced to move proximally.

U.S. Patent application publication 2004/0082915 A1, to Kadan, whose disclosure is incorporated herein by reference, describes a system for performing diagnostic needle arthroscopy and lavage through a single port of entry into the joint compartment. The system is comprised of a handpiece having valves for irrigation and suctioning, a diagnostic cannula attached to the handpiece. The system includes a mobile cart, camera, a high-resolution monitor and an air compressor to power individually controlled irrigation pumps to deliver irrigation fluid to a handpiece and a vacuum suction console to collect fluid.

U.S. Pat. No. 8,709,008, to Willis, et al., whose disclosure is incorporated herein by reference, describes visual electrode ablation systems which include a deployment catheter and an attached imaging hood deployable into an expanded configuration. In use, the imaging hood is placed against or adjacent to a region of tissue to be imaged in a body lumen that is normally filled with an opaque bodily fluid such as blood. A translucent or transparent fluid, such as saline, can be pumped into the imaging hood until the fluid displaces any blood, thereby leaving a clear region of tissue to be imaged via an imaging element in the deployment catheter. An electric current may be passed through the fluid such that it passes directly to the tissue region being imaged and the electrical energy is conducted through the fluid without the need for a separate ablation probe or instrument to ablate the tissue being viewed.

U.S. Patent application publication 20130030426 A1, to Gallardo, et al., whose disclosure is incorporated herein by reference, describes a catheter adapted for ablation which multiple dedicated irrigation tubings to supply fluid to their respective electrode or set of electrodes. The tubings provide parallel flow pathways through the catheter where irrigation fluid is delivered to irrigated tip and/or ring electrodes which can accomplish uni-polar or bi-polar ablation. Such separate and dedicated fluid pathways allow fluid to be delivered to the corresponding electrode or set of electrodes at different flow rates. An integrated ablation system using such catheter has an ablation energy source and an irrigation pump with multiple pump heads that can operate independently of each other. An integrated irrigation tubing set is included to extend between the fluid source and the catheter, with each pump head being able to act on a different tubing that delivers fluid to a different electrode or set of electrodes.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention that is described herein provides a medical pump including first and second compartments, which are configured to accept respective first and second containers of fluid to be pumped to a medical device, and a paddle, which is fitted between the first and second compartments. The pump additionally includes a control module, which is configured to drive the paddle to alternate between first time periods in which the paddle applies pressure to the first container so as to pump the fluid therefrom, and second time periods in which the paddle applies the pressure to the second container so as to pump the fluid therefrom.

In some embodiments, the medical device includes a probe including an ablation electrode that is configured to perform ablation of tissue, and wherein the probe is configured to receive the fluid and to irrigate the tissue with the received fluid during the ablation. In other embodiments, the control module is configured to sense a position of the paddle and to change a rotation direction of the paddle so as to alternate between the first and second time periods based on the position of the paddle. In yet other embodiments, the pump includes a sensor, which is configured to measure an angle of the paddle and to send the measured angle to the control module so as to alternate between the first and second time periods based on the measured angle.

In an embodiment, the control module is configured to sense a reduced flow of the fluid from the first container and to change a rotation direction of the paddle so as to alternate between the first and second time periods based on the reduced flow. In another embodiment, the pump is coupled to a flow meter, which is configured to measure the reduced flow in the first and second time periods, and to send the measured reduced flow to the control module. In yet another embodiment, the first compartment is formed from a first wall and the paddle, the second compartment is formed from a second wall and the paddle, and the paddle rotates between the first and second walls about a hinge defined by a junction of planes defining the first and second walls.

There is additionally provided, in accordance with an embodiment of the present invention, a method including providing first and second compartments, which are configured to accept respective first and second containers of fluid to be pumped to a medical device. A paddle is fitted between the first and second compartments. The paddle is driven to alternate between first time periods in which the paddle applies pressure to the first container so as to pump the fluid therefrom, and second time periods in which the paddle applies the pressure to the second container so as to pump the fluid therefrom.

The present disclosure will be more fully understood from the following detailed description of the embodiments thereof, taken together with the drawings, in which:

DETAILED DESCRIPTION OF EMBODIMENTS

Overview

Medical probes such as catheters are used in a variety of medical procedures, such as ablation of tissue in a heart. A distal end of the probe may comprise ablation electrodes, and the probe is configured to receive a fluid from an irrigation system and to irrigate the tissue with the received fluid during the ablation. Typically, such irrigation systems comprise a peristaltic irrigation pump that transports the irrigation fluid from a fluid container, through the distal end, to the tissue.

However, the inventor has found that a peristaltic pump introduces electrical noise into measurements made during the procedure. The electrical noise is probably caused by a piezoelectric effect activated by a varying pressure on tubing used in the pump. While the piezoelectric voltages are of the order of microvolts, the conductive property of the fluid (e.g., a saline solution) used for irrigation transfers these voltages to the catheter, and since cardiac voltages are also of an order of microvolts, the voltages generated by the pump interfere with the measured cardiac voltages.

Embodiments of the present invention that are described herein below provide improved techniques for transporting the fluid using a pressure-driven irrigation pump. In an embodiment, the pump comprises two compartments (denoted first and second compartments), which are configured to accept respective first and second containers of the fluid to be pumped to the distal end, and a paddle is fitted between the first and second compartments.

In some embodiments, the first compartment is formed from a first wall and the paddle, the second compartment is formed from a second wall and the paddle, and the paddle rotates between the first and second walls about a hinge defined by a juncture of the first and second walls. In other embodiments, an irrigation control module is configured to drive the paddle, typically using a motor, to alternate between first time periods in which the paddle applies pressure to the first container so as to pump the fluid therefrom, and second time periods in which the paddle applies the pressure to the second container so as to pump the fluid therefrom.

In an embodiment, the control module is configured to sense a position of the paddle and to change a rotation direction of the paddle so as to alternate between the first and second time periods based on the position of the paddle. In another embodiment, the pump comprises a position sensor, which is configured to measure an angle of the paddle and to send the measured angle to the control module so as to perform the alternation. In an alternative embodiment, the pump is coupled to a flow meter, which is configured to measure a reduced flow in the first and second time periods, and to send the measured reduced flow to the control module, so as to alternate between the first and second time periods.

System Description

Figure 1:
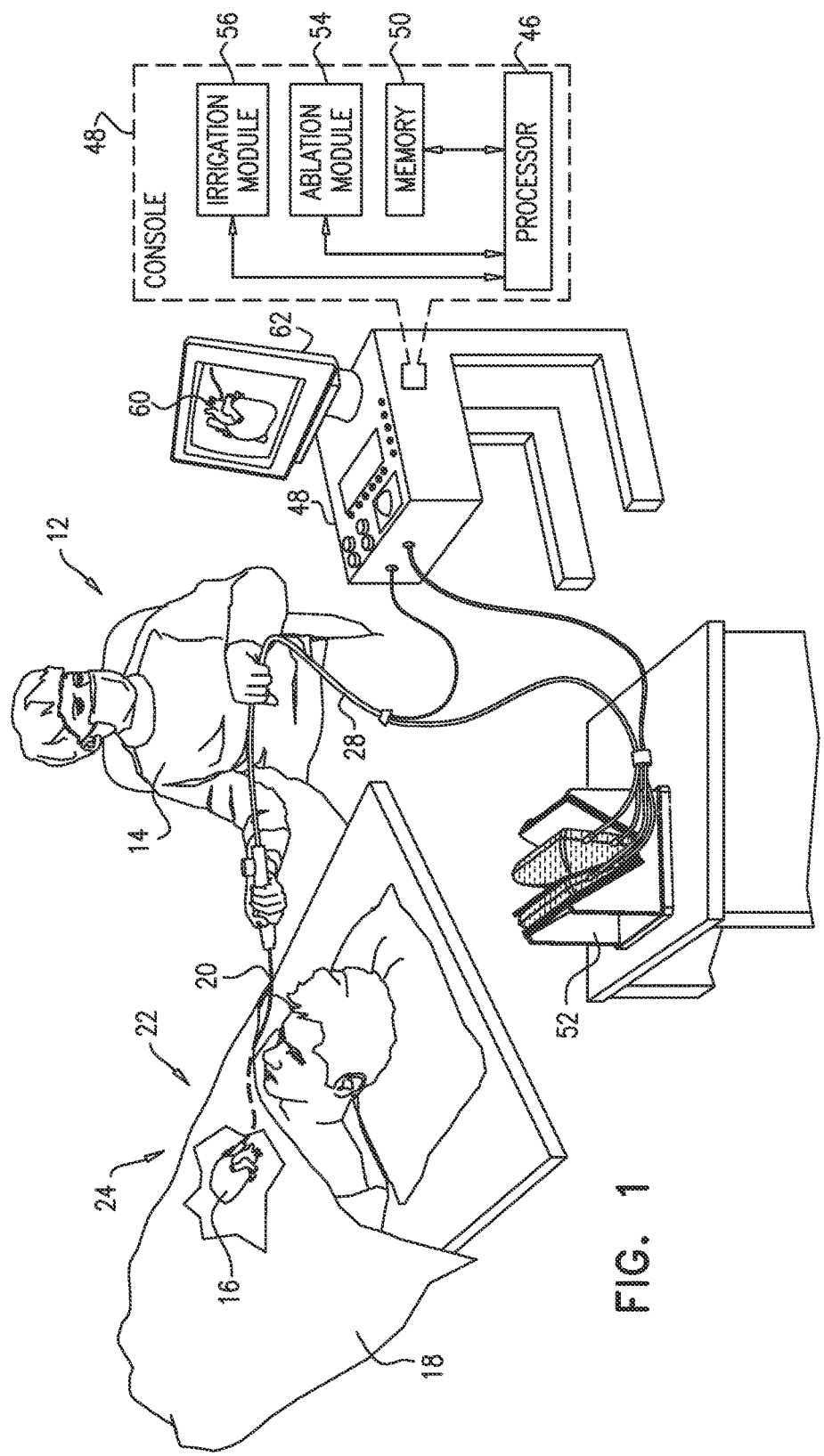
FIG. 1 is a schematic illustration of a minimally invasive medical system, in accordance with an embodiment of the present invention.

FIG. 1 is a schematic illustration of a minimally invasive medical system 12, in accordance with an embodiment of the present invention. The system may be used in a procedure that is performed by a medical professional 14, and, by way of example, system 12 is assumed to comprise an ablation procedure of a portion of a heart 16 of a human patient 18. In order to perform the ablation, medical professional 14 inserts a probe 20 into a lumen of the patient, so that a distal end 22 of the probe enters the heart of the patient. Distal end 22 comprises electrodes 24 mounted on the outside of the distal end, the electrodes contacting respective regions of the heart. Probe 20 has a proximal end 28 connected to an operating console 48 and, in parallel, to an irrigation assembly 52 that provides irrigation fluid for the ablation procedure and that is described with reference to FIG. 2.

Irrigation assembly 52 delivers the fluid into an irrigation tube 86 (shown in FIG. 2), which transports the fluid to distal end 22 during medical procedures, such as ablation. Assembly 52 is controlled by an irrigation module 56 so as to regulate the flow of the fluid to distal end 22 according to the irrigation requirements of the medical procedure. The functions of assembly 52 and module 56 are described below.

System 12 is controlled by a system processor 46 located in operating console 48 of the system. During the procedure, processor 46 typically tracks a location and an orientation of distal end 22 of the probe, using methods known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62.

In order to operate system 12, processor 46 communicates with a memory 50, and with a number of modules used by the processor to operate the system, such as an ablation module 54, an irrigation module 56 and a tracking module (not shown if FIG. 1, but which operates the tracking method used by processor 46). Ablation module 54 allows the processor to control parameters, such as the power used, of the ablation procedure. Irrigation module 56 allows processor 46 to control parameters, such as flow rate of the irrigation fluid, during ablation. For simplicity, other modules, which may comprise hardware as well as software elements, are not illustrated in FIG. 1.

Figure 2:
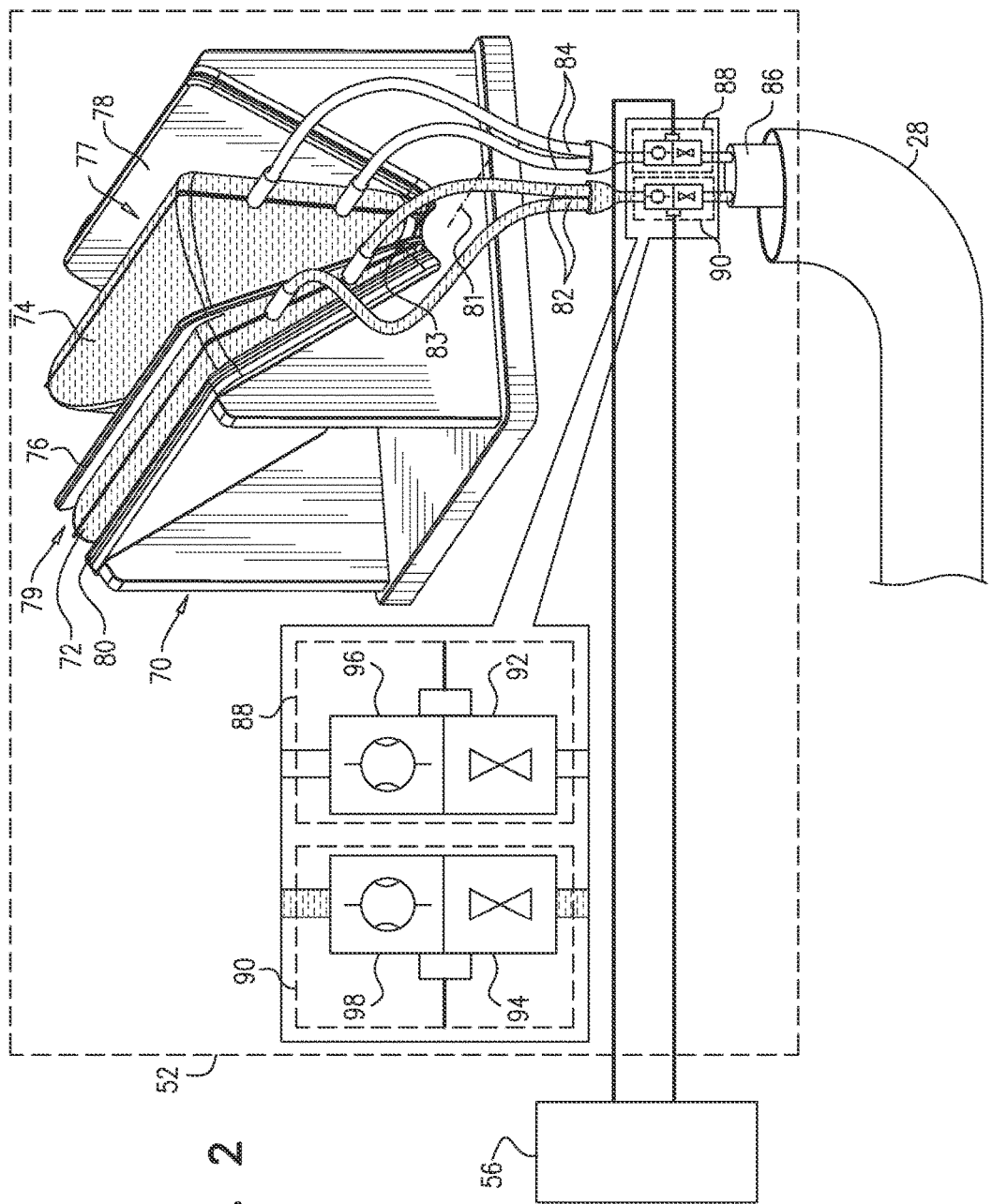
FIG. 2 is a schematic illustration of an irrigation assembly in a minimally invasive medical system, in accordance with an embodiment of the present invention.

FIG. 2 is a schematic illustration of irrigation assembly 52 in minimally invasive medical system 12, in accordance with an embodiment of the present invention.

The irrigation assembly comprises an irrigation pump 70. The pump is in the form of an open "hardcover book," and comprises two compartments formed by two walls (the two "covers" of the book) and a paddle 76 (corresponding to a page of the book) located between the walls. A right compartment 77 is formed by a first wall 78, which is the "right cover" of the "hardcover book", and paddle 76. A left compartment 79 is formed by a second wall 80, which is the "left cover" of the "hardcover book", and paddle 76. The paddle pivots about a hinge 81 parallel to a junction between planes defining walls 78 and 80, (corresponding to the "spine" of the book) and oscillates between the walls using a motor (not shown in FIG. 2). The motor is controlled by irrigation module 56, the irrigation module acting as a control module for the pump. The use of the terms "right" and "left" in the description of the pump is purely for clarity to differentiate the compartments, and it will be understood that the pump may operate in many different orientations.

In the example of FIG. 2, two fluid containers, also herein termed sacks, are placed in the right and left compartments to provide the irrigation fluid. A container 72 is placed in the left compartment, between wall 80 and paddle 76, and a container 74 is placed in the right compartment, between wall 78 and paddle 76. Each sack contains the irrigation fluid and two nipples that lead the fluid out of the sacks. A first pair of tubes 82 is connected to the nipples of sack 72 and a second pair of tubes 84 is connected to the nipples of sack 74.

In an embodiment, the two nipples of each sack are used for flow redundancy. In case one of the nipples is blocked, the other nipple of the sack directs the fluid into the respective tube. In another embodiment, each pair of tubes 82 and 84 merges into a single (wider) tube and connects to a flow control box. Tubes 82 are connected to a box 90, and tubes 84 are connected to a box 88.

Box 88 comprises a flow meter 96 and a valve 92. The flow meter measures the fluid flow in tubes 84, from sack 74 to irrigation tube 86. The valve enables the flow from sack 74 to irrigation tube 86, in an "open" state, and blocks the flow in a "close" state. Similarly, box 90 comprises a flow meter 98 and a valve 94. The flow meter measures the flow in tubes 84, from sack 72 to irrigation tube 86, and valve 94 enables the flow from sack 74 to irrigation tube 86, in an "open" state, and blocks the flow in a "close" state. In some embodiments each of the valves has the capability to regulate the flow in a tunable open state (e.g., wide open for fast flow and narrow open for slow flow). Boxes 88 and 90 are controlled by irrigation module 56, and the valves are controllable automatically (by module 56), or manually (by a medical professional).

Before an ablation procedure, paddle 76 is rotated towards one of the walls, for example towards wall 78. As a result, the left compartment (between paddle 76 and wall 80) is able to receive a new sack filled with the irrigation fluid. Thus, sack 72 may be placed in the left compartment of pump 70. At this stage both valves 92 and 94 are closed and the irrigation assembly is ready for the ablation procedure.

When the ablation procedure starts, module 56 sends a first command to open valve 94, and a second command to activate the pump motor in order to rotate paddle 76 towards the left so as to compress sack 72 and transport the fluid from sack 72 to tubes 82. At this stage, the fluid flows in tubes 82 (while tubes 84 do not contain fluid). Flow meter 98 measures the flow and sends the readings to module 56, which regulates the compression force of paddle 76 on sack 72 by controlling the force of the pump motor. The required flow at meter 98 is dictated by the ablation module, and the irrigation module sets the flow (and thus the compression force on sack 72) accordingly. In other embodiments a sensor 83 at the hinge of pump 70, can be used for measuring the angle of paddle 76 so as to control the compression on sacks 72 and 74.

As shown in FIG. 2, when most of the fluid outflows from sack 72, the right compartment is sufficiently open for placement of sack 74 (filled with irrigation fluid). When sack 72 is about to be empty, the sensor and/or flow meter 94 sends an alarm to module 56, which closes valve 94, opens valve 92, and reverses the direction of the motor in order to start compressing sack 74. At this stage the flow stops in tubes 82, and the fluid from sack 74 flows in tubes 84. Module 56 receives flow readings from flow meter 96 and angle readings from the sensor in the hinge so as to control the flow rate of the ablation procedure, by controlling the angle of paddle 76, and by controlling the degree of open state in valve 92. (Professional 14 typically sets maximum and minimum threshold values for the flow rate.) Paddle 76 is rotated to the right (towards wall 78) and an operator (or a machine) may pull out empty sack 72, and replace it with a new sack once the left compartment is sufficiently open to contain a filled sack.

The oscillation of paddle 76 allows continuous flow of irrigation fluid into the distal end during the ablation procedure, without creating electrical noise in system 12. In addition, the pump structure provides a compact mechanism to deliver an unlimited volume of irrigation fluid with tight flow control according to the irrigation flow specification of the ablation procedure.

Figure 3:
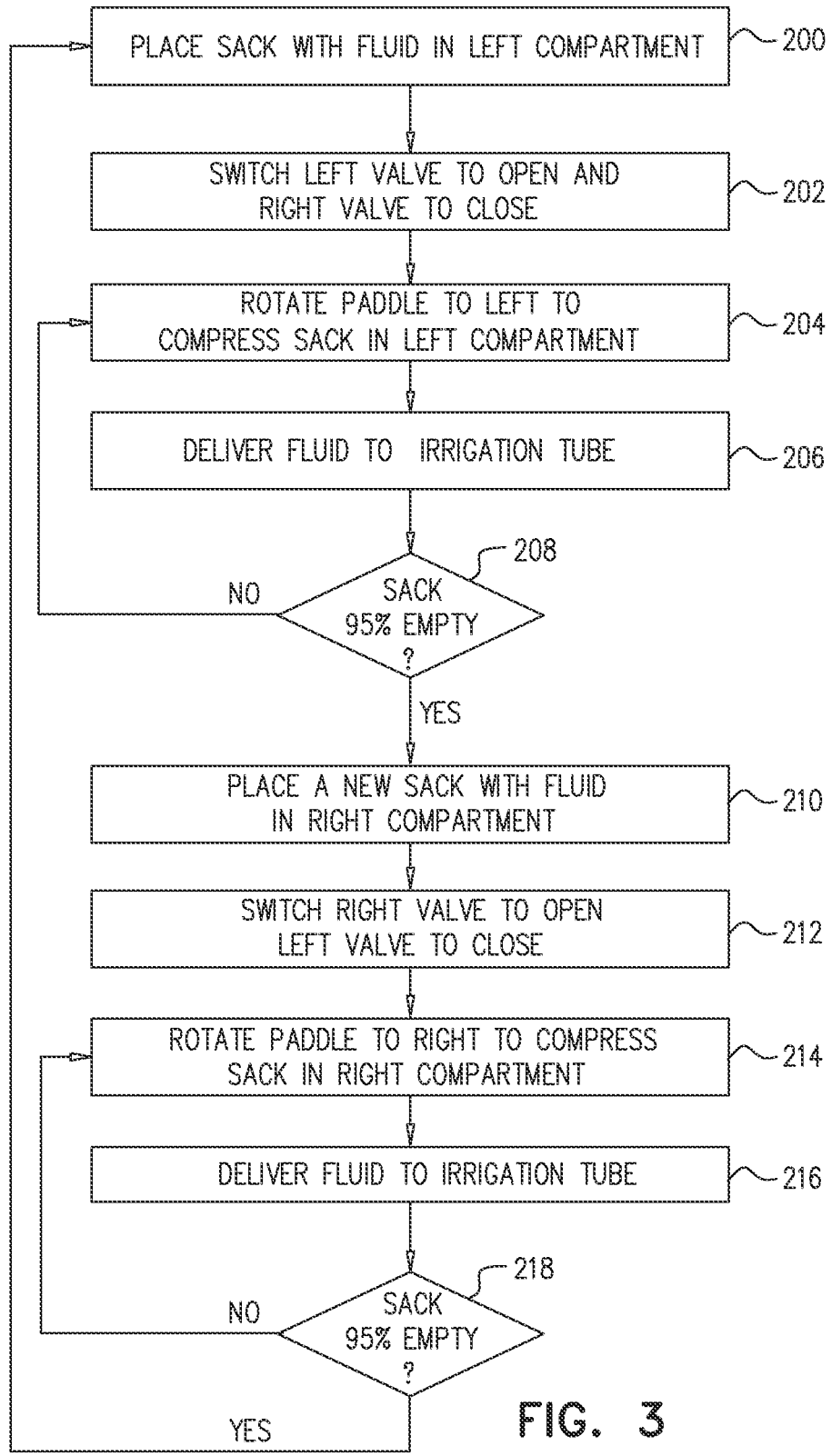
FIG. 3 is a flow chart that schematically illustrates an irrigation method in a minimally invasive medical procedure, in accordance with an embodiment of the present invention.

FIG. 3 is a flow chart that schematically illustrates an irrigation method in minimally invasive medical system 12, in accordance with an embodiment of the present invention. The method begins with placing sack 72 in the left compartment at a left sack placing step 200. At a left valve opening step 202, module 56 sets valve 94 to an open state and valve 92 to a close state in order to allow the fluid to flow from sack 72, via tubes 82, into irrigation tube 86. At a left compressing step 204, module 56 commands the motor to rotate paddle 76 to the left in order to compress sack 72. At a left delivery step 206, the irrigation fluid flows from sack 72, through tubes 82, into irrigation tube 86 and the flow rate is monitored by flow meter 98, and controlled by the measured rotation angle of paddle 76.

At a first decision step 208, module 56 checks if sack 72 is almost (e.g., 95%) empty by sensing, for example, the rotation angle of the paddle using sensor 83. The flow rate and other control values (such as the rotation angle of paddle 76) have upper and lower control limits, and crossing them triggers an alarm. If the values are within the control limits, the method loops back to compressing step 204. If at least one of the values (e.g., flow rate or measured rotation angle) cross the control limit, module 56 alarms that the sack is 95% empty, and the method continues to a right sack placing step 210, where an operator, or a machine, places a new sack (e.g., sack 74) in the right compartment of pump 70.

At a right valve opening step 212, module 56 sets valve 92 to an open state and valve 94 to a close state in order to allow the fluid flow from sack 74 via tubes 84, into irrigation tube 86. At a right compressing step 214, module 56 commands the motor to rotate paddle 76 to the right in order to compress sack 74. At a right delivery step 216, the irrigation fluid flows from sack 74, through tubes 82, into irrigation tube 86 and the flow rate is monitored by flow meter 96, and controlled by the measured rotation angle of paddle 76.

At a second decision step 218, module 56 checks if sack 74 is almost empty by sensing the angle of paddle 76 or by reading flow rates in flow meter 96. If the values are within the control limits, the method loops back to right compressing step 214 and continues to deliver the irrigation fluid from sack 74 to tubes 84. If at least one of the values crosses the its respective control limit, the method loops back to left sack placing step 200 and an operator, or a machine, places a new sack (filled with the irrigation fluid) in the left compartment to start a new irrigation cycle from the left compartment.

Inspection of the flow chart shows that during operation the pump alternates between first time periods, corresponding to the times for steps 200-206, and second time periods, corresponding to the times for steps 210-216. During the first time periods the paddle applies pressure to containers 72, in compartment 79, thus pumping fluid from these containers. In the second time periods the paddle applies pressure to containers 74, in compartment 77, and so pumps fluid from containers 74.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A system, comprising:
   a medical device comprising a probe comprising an ablation electrode configured to perform ablation of tissue, the probe being configured to receive fluid and to irrigate the tissue with the received fluid during ablation; and
   a medical pump comprising
      first and second compartments configured to accept respective first and second containers of the fluid to be pumped to the medical device,
      a paddle having a first planar surface and an opposing second planar surface, fitted between the first compartment and the second compartment and dividing the first compartment from the second compartment, and
      a control module configured to drive the paddle to alternate between first time periods in which the first planar surface of the paddle applies pressure to the first container to pump the fluid therefrom, and second time periods in which the opposing second planar surface of the paddle applies the pressure to the second container to pump the fluid therefrom.

2. The system according to claim 1, wherein the control module is configured to sense a position of the paddle and to change a rotation direction of the paddle to alternate between the first and second time periods based on the position of the paddle.

3. The system according to claim 1, wherein the medical pump further comprises a sensor, configured to measure an angle of the paddle and to send the measured angle to the control module to alternate between the first and second time periods based on the measured angle.

4. The system according to claim 1, wherein the control module is configured to sense a reduced flow of the fluid from the first container and to change a rotation direction of the paddle to alternate between the first and second time periods based on the reduced flow.

5. The system according to claim 4, wherein the medical pump further comprises a flow meter coupled to the medical pump, the flow meter configured to measure the reduced flow in the first and second time periods, and to send the measured reduced flow to the control module.

6. The system according to claim 1, wherein the first compartment is formed from a first planar wall and the first planar surface of the paddle, the second compartment is formed from an opposing second planar wall and the opposing second planar surface of the paddle, and the paddle rotates between the first and second planar walls about a hinge defined by a junction of planes defining the first and second planar walls.

7. A method of using a medical pump comprising first and second compartments configured to accept respective first and second containers of fluid to be pumped to a medical device, a paddle having a first planar surface and an opposing second planar surface, fitted between the first compartment and the second compartment and dividing the first compartment from the second compartment, and a control module configured to drive the paddle to alternate between first time periods in which the first planar surface of the paddle applies pressure to the first container to pump the fluid therefrom, and second time periods in which the opposing second planar surface of the paddle applies the pressure to the second container to pump the fluid therefrom, the method comprising:
   placing the first compartment in the first container and the second compartment in the second container; and
   driving the paddle to alternate between first time periods wherein the first planar surface of the paddle applies pressure to the first container thereby pumping the fluid from the first container, and second time periods wherein the opposing second planar surface of the paddle applies pressure to the second container thereby pumping the fluid from the second container, wherein pumping the fluid comprises irrigating a tissue with the pumped fluid during ablation of tissue.

8. The method according to claim 7, wherein alternating between first time periods and second time periods comprises
   sensing a position of the paddle, and
   changing a rotation direction of the paddle to alternate between the first and second time periods based on the position of the paddle.

9. The method according to claim 7, wherein sensing a position comprises
   measuring an angle of the paddle in the first and second time periods, and
   sending the measured angle to a control module controlling the paddle, to alternate between the first and second time periods based on the measured angle.

10. The method according to claim 7, further comprising sensing a reduced flow of the fluid, and
   changing a rotation direction of the paddle to alternate between the first and second time periods based on the reduced flow.

11. The method according to claim 10, wherein sensing a position comprises measuring the reduced flow of the fluid in the first and second time periods, and sending the measured reduced flow to a control module controlling the paddle.

12. The method according to claim 7, wherein the first compartment is formed from a first wall and the first planar surface of the paddle, the second compartment is formed from an opposing second wall and the opposing second planar surface of the paddle, and the paddle rotates between the opposing first and second walls about a hinge defined by a junction of planes defining the first and second planar walls.

13. A system, comprising:
a medical device comprising a probe comprising an ablation electrode configured to perform ablation of tissue, the probe being configured to receive fluid and to irrigate the tissue with the received fluid during ablation; and
a medical pump comprising
a first planar wall having a first top edge and a first bottom edge, and an opposing second planar wall having a second top edge and a second bottom edge, wherein a distance between the first top edge and the second top edge is greater than a distance between the first bottom edge and the second bottom edge, defining a compartment have a V-configuration;
a paddle having a first planar surface and an opposing second planar surface, the paddle being disposed between the first planar wall and the opposing second planar wall dividing the compartment into a first compartment and a second compartment, the first and second compartments configured to accept respective first and second containers of the fluid to be pumped to the medical device, and
a control module configured to drive the paddle to alternate between first time periods in which the first planar surface of the paddle applies pressure to the first container to pump the fluid therefrom, and second time periods in which the second planar surface of the paddle applies the pressure to the second container to pump the fluid therefrom.

14. The system according to claim 13, further comprising the first and second containers comprising fluid, the first container disposed in the first compartment and the second container disposed in the second compartment.

15. The system according to claim 14, wherein the medical device is in flow communication with the first container and the second container.

16. The system according to claim 13, wherein the control module is configured to sense a position of the paddle and to change a rotation direction of the paddle to alternate between the first and second time periods based on the position of the paddle.

17. The system according to claim 13, wherein the medical pump further comprises a sensor configured to measure an angle of the paddle and to send the measured angle to the control module to alternate between the first and second time periods based on the measured angle.

18. The system according to claim 13, wherein the control module is configured to sense a reduced flow of the fluid from the first container and to change a rotation direction of the paddle to alternate between the first and second time periods based on the reduced flow.

19. The system according to claim 18, wherein the medical pump further comprises a flow meter coupled to the medical pump, the flow meter configured to measure the reduced flow in the first and second time periods, and to send the measured reduced flow to the control module.

20. A method, comprising:
providing a medical pump comprising
a first planar wall having a first top edge and a first bottom edge, and an opposing second planar wall having a second top edge and a second bottom edge, wherein a distance between the first top edge and the second top edge is greater than a distance between the first bottom edge and the second bottom edge, thereby defining a compartment have a V-configuration,
a paddle having a first planar surface and an opposing second planar surface, the paddle being disposed between the first planar wall and the second planar wall dividing the compartment into a first compartment and a second compartment,
a control module configured to drive the paddle;
disposing a first container in the first compartment and the second container in the second compartment, the first and second containers comprising a fluid;
providing a medical device in flow communication with the first and second containers, the medical device comprising a probe comprising an ablation electrode configured to perform ablation of tissue, wherein the probe is configured to receive the fluid and to irrigate tissue with the received fluid during ablation; and
driving the paddle to alternate between first time periods wherein the first planar surface of the paddle applies pressure to the first container thereby pumping the fluid therefrom, and second time periods wherein the opposing second planar surface of the paddle applies pressure to the second container thereby pumping the fluid therefrom.

21. The method according to claim 20, further comprising ablating tissue of a subject.

22. The method according to claim 21, wherein pumping the fluid comprises irrigating a tissue with pumped fluid during ablation of the tissue.

23. The method according to claim 22, wherein alternating between first time periods and second time periods comprises
sensing a position of the paddle, and
changing a rotation direction of the paddle to alternate between the first and second time periods based on the position of the paddle.

24. The method according to claim 23, wherein sensing a position comprises
measuring an angle of the paddle in the first and second time periods, and
sending the measured angle to a control module controlling the paddle to alternate between the first and second time periods based on the measured angle.

25. The method according to claim 24, further comprising sensing a reduced flow of the fluid, and
changing a rotation direction of the paddle to alternate between the first and second time periods based on the reduced flow.

26. The method according to claim 25, wherein sensing a position comprises
measuring the reduced flow of the fluid in the first and second time periods, and sending the measured reduced flow to a control module controlling the paddle.

27. The method according to claim 20, wherein the opposing first and second walls rotate about a hinge defined by a junction of planes defining the first and second walls.

* * * * *